United States Patent
Manzke et al.

(10) Patent No.: US 11,304,686 B2
(45) Date of Patent: Apr. 19, 2022

(54) SYSTEM AND METHOD FOR GUIDED INJECTION DURING ENDOSCOPIC SURGERY

(75) Inventors: Robert Manzke, Husberg (DE); Raymond Chan, San Diego, CA (US); Haytham Elhawary, New York, NY (US); Aleksandra Popovic, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 769 days.

(21) Appl. No.: 14/123,547

(22) PCT Filed: Jun. 11, 2012

(86) PCT No.: PCT/IB2012/052940
§ 371 (c)(1),
(2), (4) Date: Dec. 3, 2013

(87) PCT Pub. No.: WO2012/172474
PCT Pub. Date: Dec. 20, 2012

(65) Prior Publication Data
US 2014/0142422 A1 May 22, 2014

Related U.S. Application Data

(60) Provisional application No. 61/498,062, filed on Jun. 17, 2011.

(51) Int. Cl.
*A61B 5/00* (2006.01)
*A61B 17/00* (2006.01)
(Continued)

(52) U.S. Cl.
CPC .... *A61B 17/00234* (2013.01); *A61B 1/00149* (2013.01); *A61B 1/04* (2013.01);
(Continued)

(58) Field of Classification Search
CPC .......... A61B 19/5244; A61B 2019/462; A61B 2019/507; A61B 8/0841
See application file for complete search history.

(56) References Cited

U.S. PATENT DOCUMENTS

| | | | |
|---|---|---|---|
| 5,660,185 A | 8/1997 | Shmulewitz et al. | |
| 7,155,315 B2 | 12/2006 | Niemeyer et al. | |

(Continued)

FOREIGN PATENT DOCUMENTS

| | | |
|---|---|---|
| JP | 2008018172 A | 1/2008 |
| JP | 2009106633 A | 5/2009 |

(Continued)

OTHER PUBLICATIONS

Azimian, H. et al. "Preoperative planning of robotics-assisted minimally invasive coronary artery bypass grafting". 2010 IEEE International Conference on Robotics and Automation, May 3-8, 2010, Anchorage, Alaska.

(Continued)

*Primary Examiner* — Joel F Brutus (57) ABSTRACT

A guidance system and method include a real-time imaging device (121) configured to intra-operatively collect image data of a target region to provide a real-time image. A target determination module (108) is configured to generate an overlay map (111) registered to the real-time image to project morphological feature information on corresponding features in the real-time image of the target region. A medical instrument (122) is provided to perform a procedure on the target region such that the at least one medical instrument is guided to a region suitable for performing an operative task based upon the overlay map.

30 Claims, 7 Drawing Sheets

(51) Int. Cl.
*A61B 34/20* (2016.01)
*A61B 34/30* (2016.01)
*A61B 34/10* (2016.01)
*A61B 1/00* (2006.01)
*A61B 1/04* (2006.01)
*A61B 5/06* (2006.01)
*A61B 8/08* (2006.01)
*A61B 8/12* (2006.01)
*A61B 17/34* (2006.01)
*A61B 90/00* (2016.01)

(52) U.S. Cl.
CPC ............ *A61B 5/061* (2013.01); *A61B 5/4839* (2013.01); *A61B 8/0841* (2013.01); *A61B 8/0883* (2013.01); *A61B 8/12* (2013.01); *A61B 17/3478* (2013.01); *A61B 34/10* (2016.02); *A61B 34/20* (2016.02); *A61B 34/30* (2016.02); *A61B 90/361* (2016.02); *A61B 2017/00119* (2013.01); *A61B 2017/00243* (2013.01); *A61B 2017/00247* (2013.01); *A61B 2034/107* (2016.02); *A61B 2034/2048* (2016.02); *A61B 2034/2059* (2016.02); *A61B 2090/062* (2016.02); *A61B 2090/065* (2016.02); *A61B 2090/363* (2016.02); *A61B 2090/365* (2016.02)

(56) References Cited

U.S. PATENT DOCUMENTS

| | | | |
|---|---|---|---|
| 7,877,128 | B2 | 1/2011 | Schwartz |
| 8,348,861 | B2 | 1/2013 | Glozman et al. |
| 2003/0007598 | A1 | 1/2003 | Wang et al. |
| 2003/0097060 | A1 | 5/2003 | Yanof et al. |
| 2004/0132006 | A1* | 7/2004 | O'Donnell et al. ............ 435/4 |
| 2004/0153128 | A1 | 8/2004 | Suresh et al. |
| 2004/0247165 | A1 | 12/2004 | Nishiura |
| 2005/0015005 | A1 | 1/2005 | Kockro |
| 2005/0159798 | A1* | 7/2005 | Graumann ......... A61B 18/1492 607/101 |
| 2006/0041243 | A1* | 2/2006 | Nayak ................ A61B 17/0206 604/506 |
| 2008/0249467 | A1* | 10/2008 | Burnett .................. A61B 1/313 604/117 |
| 2009/0048525 | A1 | 2/2009 | Rogers et al. |
| 2009/0118609 | A1* | 5/2009 | Rahn ....................... A61B 6/12 600/411 |
| 2009/0149867 | A1 | 6/2009 | Glozman et al. |
| 2010/0312095 | A1* | 12/2010 | Jenkins .................. A61B 5/415 600/411 |
| 2010/0331619 | A1 | 12/2010 | Miyoshi et al. |
| 2011/0087088 | A1 | 4/2011 | Korn et al. |
| 2011/0202012 | A1* | 8/2011 | Bartlett ........................ 604/218 |
| 2014/0037088 | A1 | 2/2014 | Suzaki et al. |

FOREIGN PATENT DOCUMENTS

| | | |
|---|---|---|
| JP | 2010200894 A | 9/2010 |
| WO | 2010086861 A1 | 8/2010 |
| WO | 2010130056 A1 | 11/2010 |
| WO | 2011057260 A2 | 5/2011 |

OTHER PUBLICATIONS

Cleary, K. et al. "Image-guided interventions: Technology Review and Clinical applications". Annual Review of Biomedical Engineering, vol. 12, pp. 119-142, 2010.

Stamm, C. et al. "Autologous bone-marrow stem-cell transplantation for myocardial regeneration". Research Letters. The Lancet, vol. 361, No. 9351, pp. 45-46, 2003.

Amado, L. et al. "Cardiac repair with intramyocardial injection of allogeneic mesenchymal stem cells after myocardial infarction". PNAS. Aug. 9, 2005, vol. 102, No. 32, pp. 11474-11479.

Stamm, C. et al. "Intramyocardial delivery of CD133+ bone marrow cells and coronary artery bypass grafting for chronic ischemic heart disease: Safety and efficacy studies". The Journal of Thoracic and Cardiovascular Surgery, Mar. 2007, vol. 133, No. 3, pp. 717-725.

Martens, T. et al. "New Technology for Surgical coronary Revascularization". Circulation, vol. 114, No. 6, 2006, pp. 607-614.

\* cited by examiner

SYSTEM AND METHOD FOR GUIDED INJECTION DURING ENDOSCOPIC SURGERY

CROSS-REFERENCE TO PRIOR APPLICATIONS

This application is the U.S. National Phase application under 35 U.S.C. § 371 of International Application Serial No. PCT/IB2012/052940, filed on Jun. 11, 2012, which claims the benefit of U.S. Application Ser. No. 61/498,062, filed on Jun. 17, 2011. These applications are hereby incorporated by reference herein.

This disclosure relates to medical procedures and systems, and more particularly to guided injection systems and methods.

Intra-myocardial stem cell injection during coronary artery bypass grafting (CABG) has a positive effect on heart regeneration. Minimally invasive endoscopic CABG (MI-CABG) is a promising and growing alternative for many patients otherwise having to undergo open chest surgery. Intra-myocardial injection of stem cells or other agents during MI-CABG may be a part of the therapy, but is technically problematic to execute successfully.

Manual intra-myocardial injection of agents during MI-CABG is challenging due to a lack of information about the extent and location of scar, ischemia or other region of pathology as well as other missing data, such as, cardiac wall thickness. The lack of information is due in part to the fact that the only intraoperative imaging modality available during MI-CABG is endoscopy.

In accordance with the present principles, a guidance system and method include a real-time imaging device configured to intra-operatively collect image data of a target region to provide a real-time image. A target determination module is configured to generate an overlay map registered to the real-time image to project morphological feature information on corresponding features in the real-time image of the target region. A medical instrument is provided to perform a procedure on the target region such that the at least one medical instrument is guided to a region suitable for performing an operative task based upon the overlay map.

A workstation includes a processor and memory coupled to the processor. A real-time imaging device is configured to intra-operatively collect image data of a target region to provide a real-time image. A target determination module is stored in the memory and configured to generate an overlay map registered to the real-time image on a display to project morphological feature information on corresponding features in the real-time image of the target region. A medical instrument is manually or automatically controlled to perform a procedure on the target region such that the at least one medical instrument is guided to a region suitable for performing an operative task based upon the overlay map.

A method includes determining characteristics of interest for a target region of a patient; real-time imaging the target region to provide a real-time image; generating an overlay map registered to the real-time image on a display to project morphological feature information on corresponding features in the real-time image of the target region; and performing a procedure on the target region such that at least one medical instrument is guided to a region suitable for performing an operative task based upon the overlay map.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

The present principles provide an injection device, systems and methods for guiding the device to a correct location in a patient, and systems and methods for retrieval and visualization of anatomical information in endoscope images. In one embodiment, an injection needle is employed which can be extended or deployed with a controlled depth depending on a local heart wall thickness or other pathology to avoid tamponade or other serious complications. The injection device would be guided and extended/deployed using sufficient feedback to an interventionalist to avoid catastrophic complications.

An endoscopic image guidance system is provided, which projects registered data about scar location and tissue thickness during minimally invasive coronary artery bypass grafting (MI-CABG) and other procedures. The injection device can be steered either manually or robotically to a target region. The injection needle is extended based on knowledge of the tissue thickness in the target region and visualization thereof. Closed-loop agent delivery during MI-CABG is possible either with semi- or fully-automated actuation of the needle and injector. Agents may include stem cells, medications, etc.

It also should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, heart, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 1:
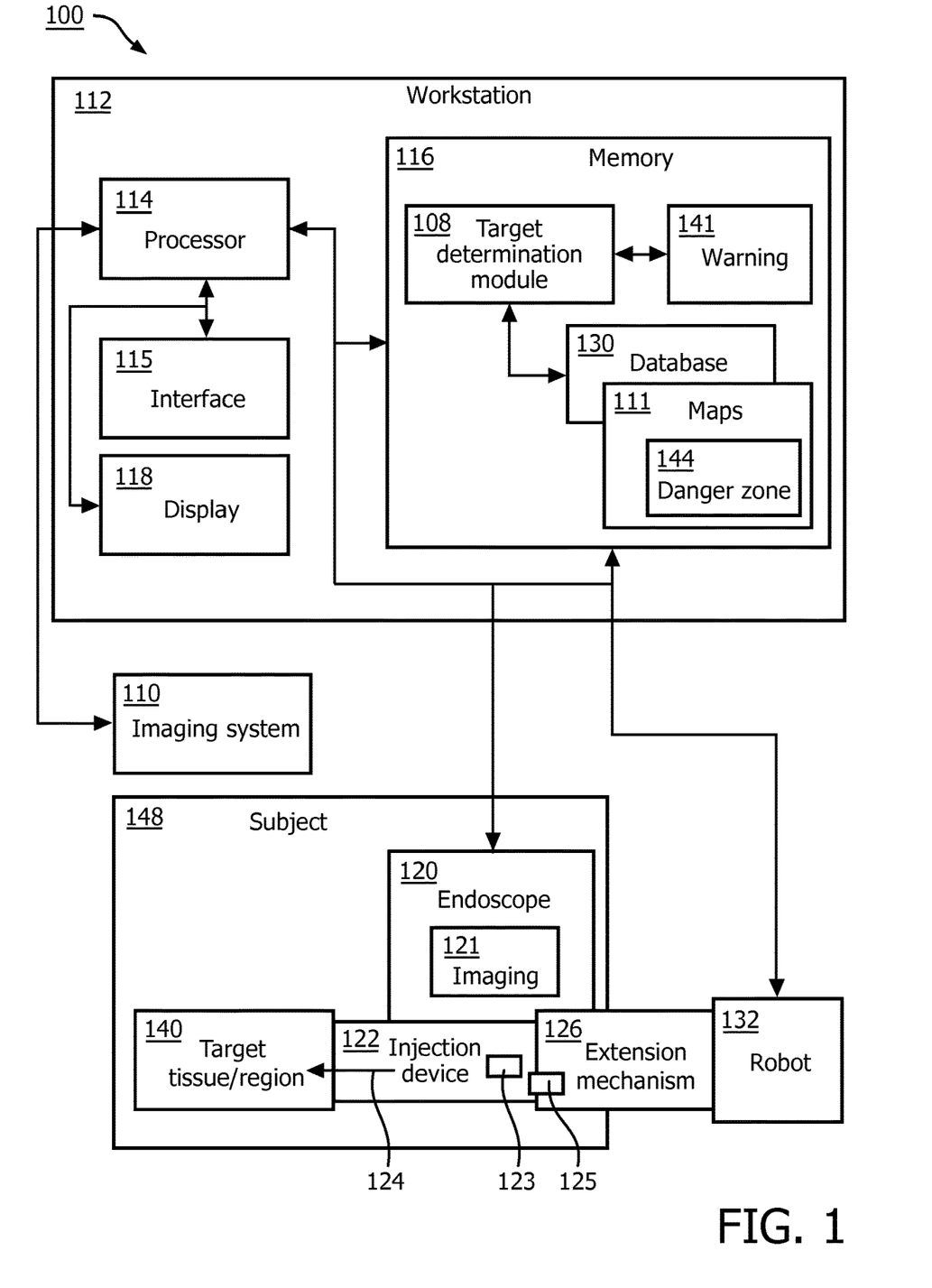
FIG. 1 is a block/flow diagram showing a system/method for guidance in accordance with an overlay map of tissue characteristics in accordance with one illustrative embodiment.

Referring now to the drawings in which like numerals represent the same or similar elements and initially to FIG. 1, a system 100 for performing a medical procedure in accordance with the present principles is illustratively depicted. System 100 may include a workstation or console 112 from which a procedure is supervised and managed. Workstation 112 preferably includes one or more processors 114 and memory 116 for storing programs and applications. Memory 116 may store programs/applications/data for guidance of medical instruments, pathology maps and related data, imaging information, etc.

The system 100 may include an endoscopic or other device 120 for gathering image data. Device 120 may include an imaging system 121 (e.g., a camera) which provides real-time image data. The endoscope 120 may include a light source to provide light during a procedure. An imaging system 110 may be employed to pre-operatively or intra-operatively project registered data of a target pathology location (or other characteristics, such as tissue thickness, etc.) during a procedure (e.g., during a MI-CABG procedure) for a target tissue or organ 140. The imaging system 110 may include, but is not limited to Computed Tomography, Magnetic Resonance Imaging, X-ray, X-ray angiography, etc.

The registered data are preferably registered with the real-time image, and the registered data and the real-time image are displayed together. The registered data may include a map.

A medical device 122 for performing the procedure may include a needle, a catheter, an electrode, an endoscope, etc. In one embodiment, device 122 includes an injection device that may be deployed by the endoscope 120 or deployed separately of the endoscope 120. The injection device 122 is preferably steerable robotically or manually to the target region 140. The injection device 122 includes an injection needle 124 or similar device and has a controlled extension mechanism 126. The injection needle 124 is extended based on knowledge of morphology, composition, physiological function and dynamics including tissue thickness, stiffness characteristics (with can vary depending on presence of fatty infiltrate, tumor, fibrous scar, etc.) in the target region 140. Such information is stored in a database 130 or in memory 116.

A closed-loop agent delivery system or robot 132 (e.g., for MI-CABG) may also be included. The delivery system 132 may include the mechanism 126, injection device 122 and needle 124. Other configurations are also contemplated. The delivery system 132 may employ a visual display, audible feedback or other haptic cues for manual operation by a physician and/or options for either (semi)-automated or automatic control. The delivery system 132 may be employed with the endoscope 120 (e.g., using a working channel in the endoscope 120) or separate from the endoscope 120 (e.g., thorough a separate instrument port).

In accordance with one embodiment, the target region 140, such as a heart, may be the subject of pathological/ morphological/physiological mapping. The mapping may include the use of one or more medical imaging devices or systems 110. The imaging system 110 may include, e.g., a magnetic resonance imaging (MRI) system, a fluoroscopy system, a computed tomography (CT) system, etc. The mapping may be obtained a priori or intra-operatively to discover and store information for the target region 140. This information may include morphology, composition, physiology and dynamics including tissue thickness, stiffness characteristics (which can vary depending on the presence of fatty infiltrate, a tumor, fibrous scar tissue, etc.) in the target region. The mappings are stored in the memory 116 and/or the database 130.

The injection device 122 may include, e.g., a catheter, a guide wire, an endoscope, a probe, a robot, an electrode, a filter device, a balloon device, or other medical component, etc. The injection device 122 may include the needle 124, which may be deployed to extend in accordance with the mapping information. As noted, the injection device 122 and the endoscope 120 may be employed as one unit or as separate units. Other instruments and tools may be employed in addition to or instead of those described.

Workstation 112 may include a display 118 for viewing internal images of a subject, and the display 118 may also permit a user to interact with the workstation 112 and its components and functions. This is further facilitated by an interface 115 which may include a keyboard, mouse, a joystick or any other peripheral or control to permit user interaction with the workstation 112.

Imaging system 110 may be provided for collecting pre-operative imaging data and/or real-time intra-operative imaging data. The pre-operative imaging may be performed at another facility, location, etc. in advance of any procedure. These 3D images may be converted to morphology maps 111 and stored in memory 116 and/or database 130.

In particularly useful embodiments, device 120 may be employed to observe the target region 140, e.g., a heart. The target region 140 may include a lesion, injury site, object or other target feature. During a procedure, morphology information previously or concurrently collected is employed to generate a virtual morphology image that can be overlaid on a real-time image collected by imaging device 121 and rendered on display 118. The virtual image is registered with the intra-operative imaging data to provide a user with information needed to perform the operation. For example, tissue thicknesses, scar tissue locations, tissue density, etc. will be indicated in the virtual image by employing textures or colors to display particular characteristics as selected or programmed by the user.

Memory 116 includes a target determination module 108. The target determination module 108 computes a location or locations where an operative procedure may be carried out based upon the mapping information stored in the memory 116 or database 130. Expert knowledge from prior cases can be encoded in database 130 for procedure optimization. For example, if device 122 includes an ablation electrode, a target may be generated in the virtual image which may be targeted for alignment manually or robotically as a procedure treatment site, e.g., a site where tissue is to be ablated based upon the morphology data. The display 118 may be employed to display both the virtual image and the real-time images such that the virtual image acts as a guidance tool for furthering the procedure.

Another aspect of the present system 100 includes providing a visual depiction of danger zones 144 corresponding to high risk areas where critical anatomy is present that should or must be avoided by the device 122 (e.g., when deploying injection needle 124) during a procedure. These structures can be identified based on patient specific information from pre-procedural imaging or from anatomical libraries of such information that can be mapped into the patient-specific coordinate space visualized endoscopically. The mapping may be performed automatically or manually using the interface 115. For example, a physician or other user may access an image and may overlay an image or pixel map over sensitive or critical areas, which need to be avoided.

The danger zone information 144 may be incorporated into a procedural confidence/complication spatial map which is used as input to computer-aided path planning and procedure optimization. In one embodiment, when a crosshair or other target symbol coincides with these danger zone regions, a warning light, sound, or other warning mechanism 141 may be triggered to alert the physician that the device (e.g., needle) should not be fired at that location(s).

In a particularly useful embodiment, a path plan may be executed in a semi-automated or automated fashion based on closed-loop control of robotic actuation of any or all devices, e.g., the injector, the needle, the endoscope, auxiliary sensing probes, etc. In one embodiment, the robot 132 is controlled manually or automatically to position device 122 with a needle 124, etc. in place. The robot 132 may employ the maps 111 stored in memory 116 to determine a best area to carry out the procedure. The target determination module 108 computes a best area using the danger zone map 144 (and other maps) determined automatically or created manually by a user. The robot 132 may be employed to guide the injection device 122 to a location and to deploy the needle 124 in accordance with depth or force feedback. The robot 132 may be controlled to position the injection device 122 using the extension mechanism 126 and information from maps 111 including the tissue data for determining acceptable positions for carrying out a procedure by module 108. The robot 132 guides the injection device 122 to an appropriate position and fires the needle 124. It should be understood the guidance and firing tasks may be employed with the manual assistance by a user. For example, a user may perform the guidance, but not the firing or vice versa.

The robot or closed loop system 132 may measure depth and force information and employed the same as feedback for controlling injection depth of needle 124. The force may be measured by a sensor 123 and the depth may be measured by translation of a motor/server 125 in the injection device 122 of other component. The force, depth or other parameters may be displayed on display 118 in real-time to assist the user during the procedure.

The present system 100 extends beyond cardiac interventions and may be applied to other procedures. For example, the present principles apply to endoscopically-guided structural heart procedures (e.g., valve repair, patent foramen ovale closure, etc.), endoscopically-guided epicardial electrode lead placement for cardiac resynchronization therapy, endoscopically-guided epicardial ablation procedures, endoscopically-guided abdominal interventions, Natural Orifice Translumenal Endoscopic Surgery (NOTES) procedures, interventional oncology, interventional neuroradiology, interventional pain procedures, etc.

Figure 2:
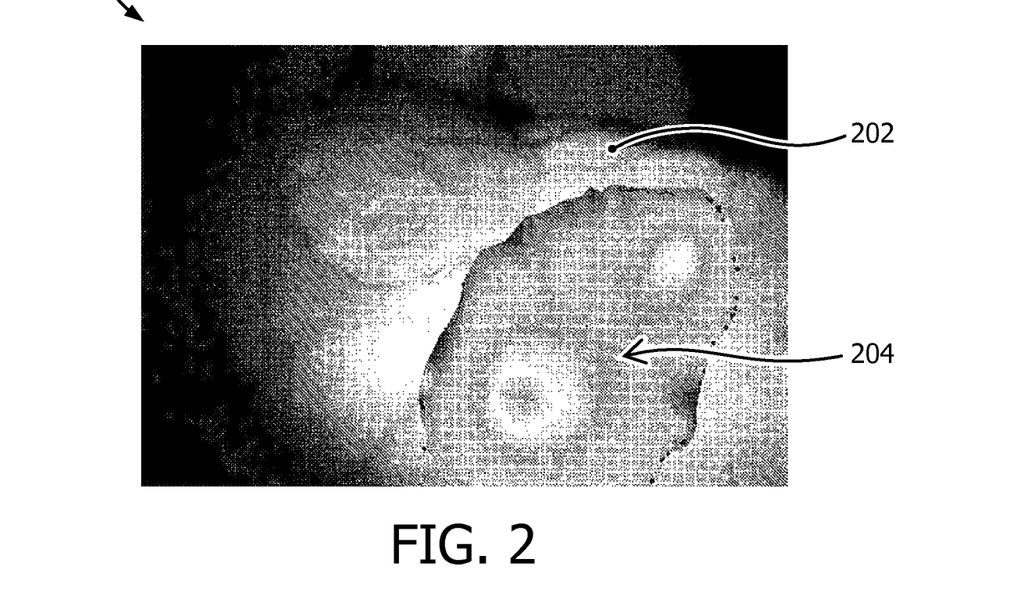
FIG. 2 is a real-time image collected by an endoscope showing an overlay map in accordance with one illustrative embodiment.

Referring to FIG. 2, an internal target image 200 shows a perspective view of a heart 202 as imaged by an endoscope with a camera. This embodiment describes a system/method to provide a digital overlay 204 over the heart 202 or a portion of the heart 202. In one example, the overlay 204 indicates cardiac wall thickness, scar/ischemia or other pathologic information about a selected region. The wall thickness or other characteristics may be indicated by textures, colors, shading or other visual effects (flashing, blinking, color changing, animation, etc.). Advantageously, the virtual image 204 is registered to the heart 202 to ensure that the information in the virtual image 204 corresponds directly with the positions of the heart 202. The virtual image 204 is preferably shown overlaid over intra-operative real-time endoscope images as depicted in FIG. 2. In this way, direct guidance data is available to a clinician/physician to make real-time decisions regarding the procedure. The virtual image 204 is preferably updated for every frame of live data.

A transformation between an endoscope coordinate system and preoperative 3D images is established by employing registration methods (e.g., using reference markers, defining origins, etc.). The preoperative 3D images may include, e.g., computed tomography (CT), magnetic resonance (MR), positron emission tomography (PET) or other imaging technologies. The surface of the heart 202 as seen in the endoscope images is enhanced with, e.g., wall thickness information indicated by the overlay 204. An acceptable needle depth may be determined, and a location that can accommodate that needle depth can be selected for injection. The thickness can be indicated by correlating colors and shades of colors to show the changing wall thicknesses with position. Other morphometric/compositional/functional information relevant to the intervention at hand may also be visualized in a similar fashion. Note that more than one characteristic may be present in the virtual image 204. For example, scar tissue may be indicated by cross-hatched regions while the wall thickness may rely of a color spectrum to show variations.

Figure 3:
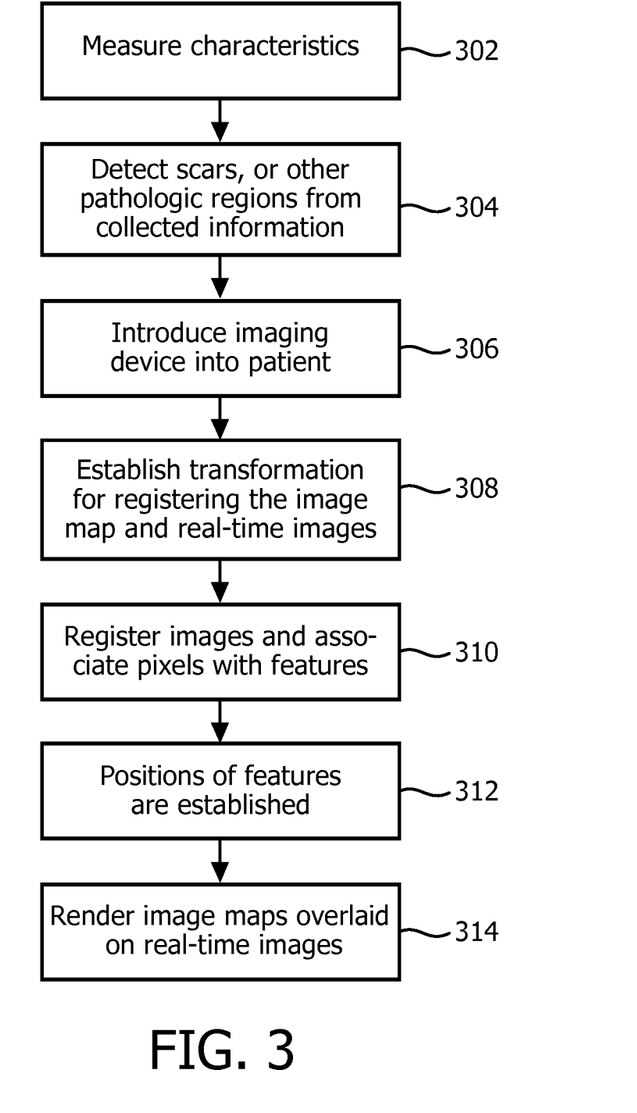
FIG. 3 is a block/flow diagram showing a guidance system/method in accordance with another illustrative embodiment.

Referring to FIG. 3, a method for exploiting visual imaging benefits in accordance with the present principles is illustratively shown. In block 302, characteristics of interest are measured, e.g., cardiac wall thickness, from a 3D heart surface reconstructed from 3D medical imaging study (CT, MRI, ultrasound (US), etc). This may be done in advance of a procedure or in some cases may be performed concurrently. This depends on the type of information being collected and the types of imaging or other tools available. In block 304, scar/ischemic/pathologic regions, etc. from the imaging study are detected from the collected information. These features will become part of a mapping of the surface of a target region but are also useful guideposts for reregistering these features as will be described.

In block 306, an endoscope or other imaging device is introduced into a patient for imaging the target region in real-time. Images of the target regions are collected. In block 308, an endoscope/target surface transformation is established by registration of the image map (virtual image) with the actual images of the target region. This may be performed using one or more different registration techniques. These techniques may employ physical features collected in the map data being correlated to visual images, etc.

In block 310, registration is provided, and feature associations with each pixel in the visual image may be made. For example, wall thickness of a heart may be established in every pixel of the endoscope image using the measured characteristics and the transformation. In block 312, scar region positions or other features may be established in endoscope images using the measured characteristics and the transformation. In block 314, the registered virtual image/endoscopic images are visualized by overlaying the virtual image or map information on the endoscope image.

Figure 4:
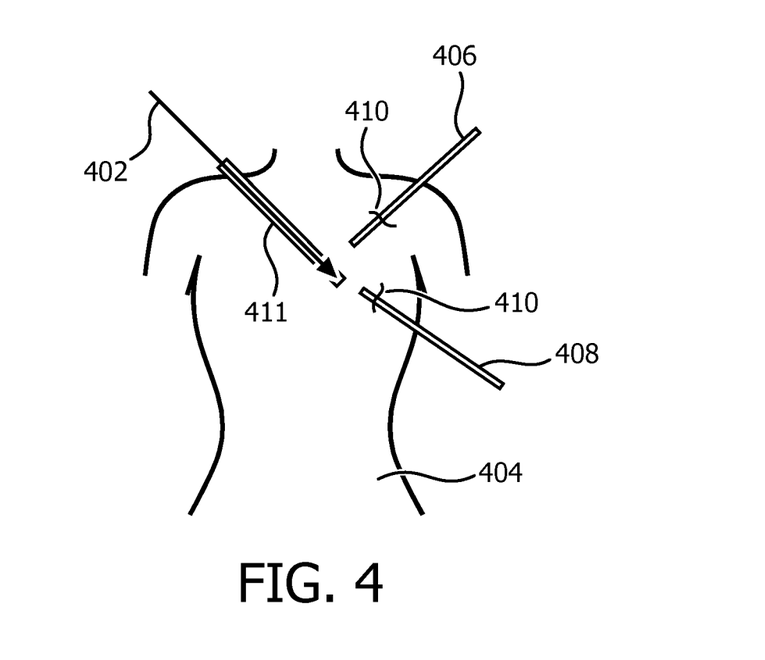
FIG. 4 is a schematic diagram illustratively showing a procedure being performed in a chest cavity using multiple instruments in accordance with another illustrative embodiment.

Referring to FIG. 4, a schematic diagram illustratively shows a procedure for a needle injection deployed through an instrument port. This embodiment is an extension of the embodiments described with reference to FIGS. 2 and 3. An endoscope 402 is inserted into a patient 404. In addition, other instruments 406, 408 may be employed. The additional instruments 406, 408 may be inserted into a patient's chest cavity through different entry points or instrument ports 410 other than an instrument port 411 for the endoscope 402.

Figure 5:
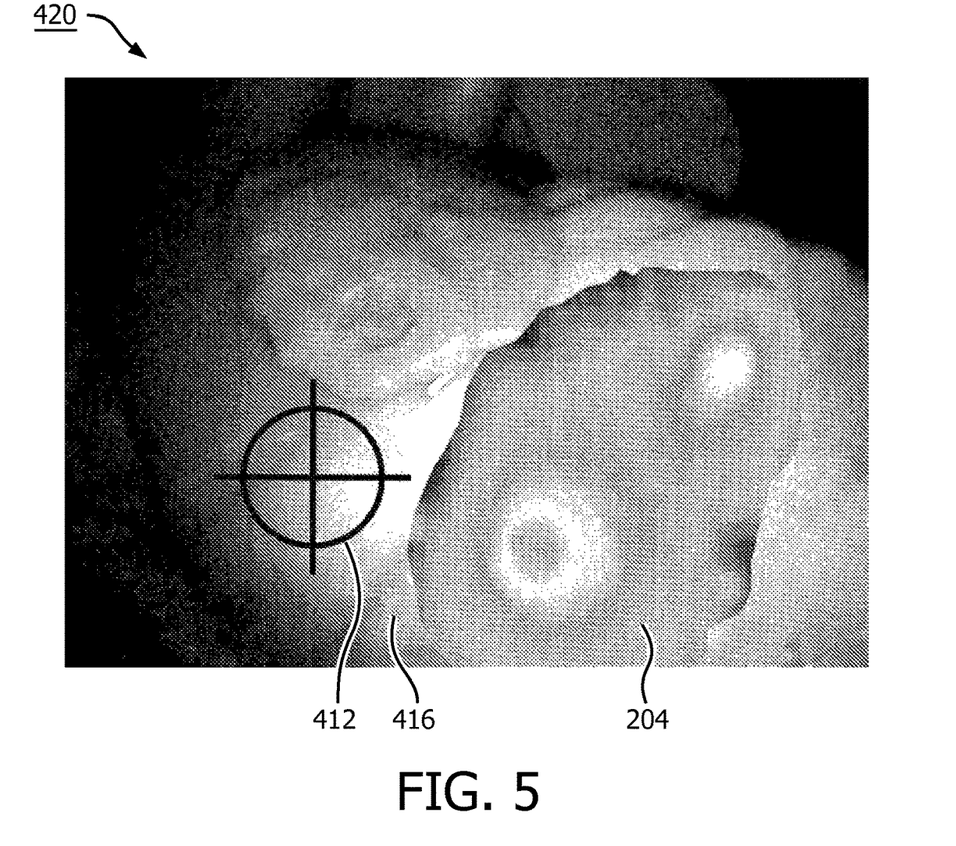
FIG. 5 is a real-time image showing a cross-hair relative to an overlay map in accordance with another illustrative embodiment.

Referring to FIG. 5 with continued reference to FIG. 4, given that a location of the instrument port 410 or 411 is known with respect to the endoscope 402 (e.g., lateral, concentric, with a fixed known mechanical coupling, etc.) then a cross hair 412 or other mark can be overlaid on an image 420 indicating a projection of an axis of the instrument port 410, 411 onto anatomical structures 416 in the endoscope image 420. This will indicate the expected trajectory of an instrument, such as a needle or the like, if inserted into a channel through the endoscope 402 or through any of the other instrument port 410.

The image 420 also includes the map 204 as described with reference to FIG. 2. The map 204 and cross-hair 412 may be concurrently displayed such that the overlay data in overlay 204 may be employed to select an operative site and aim an instrument using the cross-hair 412.

Figure 6:
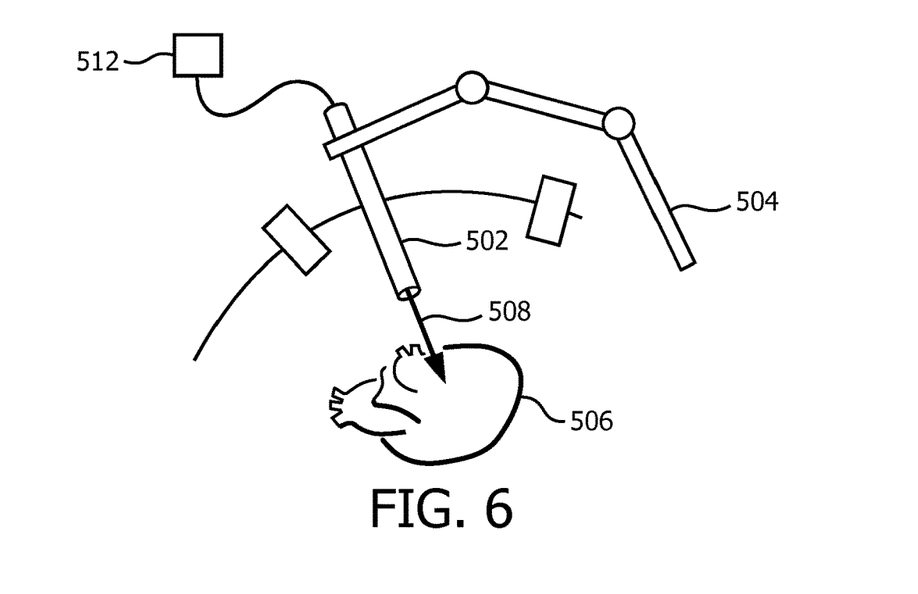
FIG. 6 is a schematic diagram illustratively showing a procedure being performed in a chest cavity using a robot in accordance with another illustrative embodiment.

Referring to FIG. 6, another embodiment is particularly useful for cases in which an endoscope 502 is held by a robot 504. If an area of interest 506 is not visible in a current endoscope view, the endoscope 502 may be steered by the robot 504 using surface information provided in the maps or preoperative images and known geometrical relationships between the heart surface and the robot, derived from the previously described registration. Additionally, the robot 504 can be steered using a visual servicing method where regions of wall thickness or ischemic/scar/pathologic tissue can be identified on pre-operative images and through registration and employed to maneuver the robot 504 to a desired location.

Another embodiment includes an injection needle 508 that is deployed through an instrument port. The injection needle 508 may be deployed through a working channel of the robotically guided endoscope 502 or may be spatially calibrated to the robotic endoscope 502 with a rigid mechanical coupling. The injection needle 508 may be guided using endoscopic images and may be deployed by the robot 504. This method may significantly improve accuracy of the needle placement, because the robot 504 can precisely control the depth of insertion of the needle 508 or other instrument.

Figure 7:
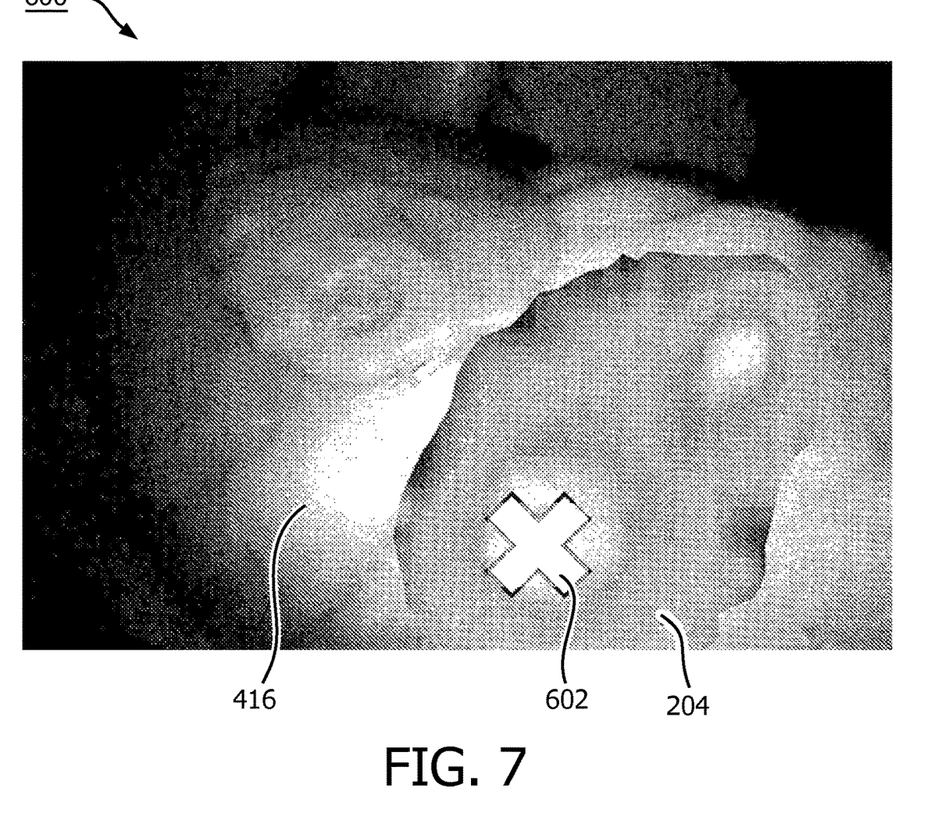
FIG. 7 is a real-time image showing a target symbol relative to an overlay map in accordance with another illustrative embodiment.

Referring to FIG. 7 with continued reference to FIG. 6, an endoscopic image 600 depicts a target region 416 such as a heart having a virtual image 204 overlaid thereon. An instrument port location provides a cross-hair or other mark 602 as an injection site. The target 602 is digitally rendered on the image 600 to provide a visual indication of where a manual or robotically controlled advance of the needle should occur. The user selects the point of insertion 602 and a depth of insertion and the robot 504 may be employed to deploy the needle 508 or other tool. The injection may then be carried out by the user.

In another embodiment, the robot 504 can position and orient the needle 508, and insertion/deployment is performed by the surgeon. As the needle 508 is being inserted, the robot or robotic system 504 can sense the depth of insertion n, e.g., from motor encoders, which can be processed by the workstation (112 in FIG. 1) and overlaid on the endoscope image 600 in display (118). The display (118) may include a distance of the needle 508 from an outer heart surface, inner heart surface, or distance from a planned depth.

In yet another embodiment, the robot 504 can insert the needle 508 or can orient the needle 508 for the surgeon to drive the instrument into the heart surface. In one case, a sensor 512, such as a force sensor or a strain/shape sensor to measure tissue deflection is/are employed to detect when the needle 508 is passing through layers of different tissue. When tissue stiffness increases or decreases, this information can be processed by the workstation (112) and overlaid or displayed on the endoscope image 600 or other area of the display. This force information can also be used as part of a closed loop system in which the robot drives the needle up to a certain transition or value of resistive force.

Figure 8:
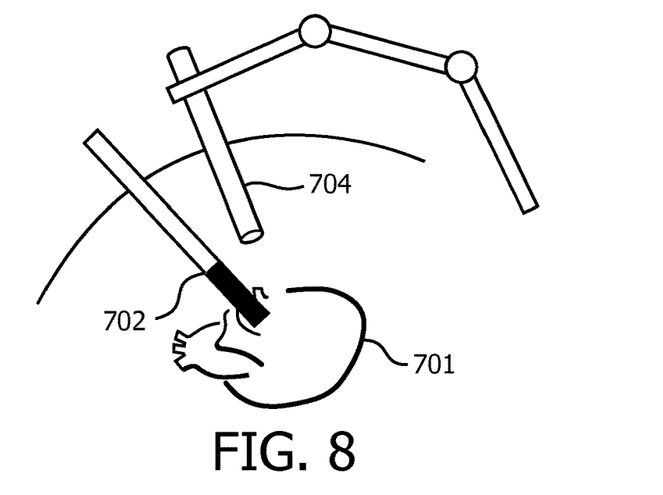
FIG. 8 is a schematic diagram illustratively showing a procedure being performed in a chest cavity using a robot and an ultrasonic imaging system for concurrently determining characteristics of the target tissue in accordance with another illustrative embodiment.

Referring to FIG. 8, in another embodiment, tissue characteristics or maps may be obtained intra-operatively. For example, a heart wall 701 thickness may be obtained intra-operatively using ultrasound measurements. The ultrasound measurement can be obtained by introducing an ultrasonic probe 702 to collect ultrasonic images.

It should be understood that other imaging technologies may also be employed. For example, the device 702 for morphometric/functional probing may be based on interrogation with spectroscopy or imaging such a diffuse optical tomography, optical coherence tomography, photoacoustics, radiation count detection (e.g., miniature Gamma camera), etc. in place of, or in addition, to ultrasound technology.

In the present example, the ultrasonic images may be matched with endoscope images obtained simultaneously via a second imaging device 704 (e.g., carried within the endoscope), such as a probe, a camera, a transducer element, etc. The imaging device images are calibrated to determine their spatial relationship relative to each other and the endoscopic camera projection. Methods for ultrasound measurements of thickness and the like are known in art. For example, using simplest A-mode US, reflection of an outer surface of the heart can be detected which can be used as an indication of the wall thickness.

To facilitate device (e.g., needle) placement, thickness information obtained from ultrasound measurements should be displayed on the endoscope images. As the ultrasound device 702 is moving on the heart surface 701, the ultrasound device 702 can be tracked on endoscope images using photogrammetric methods known in art. Thus, the position of the device 702 with respect to the images is known, and measurement data can be overlaid as shown, e.g., in FIG. 2.

Figure 9:
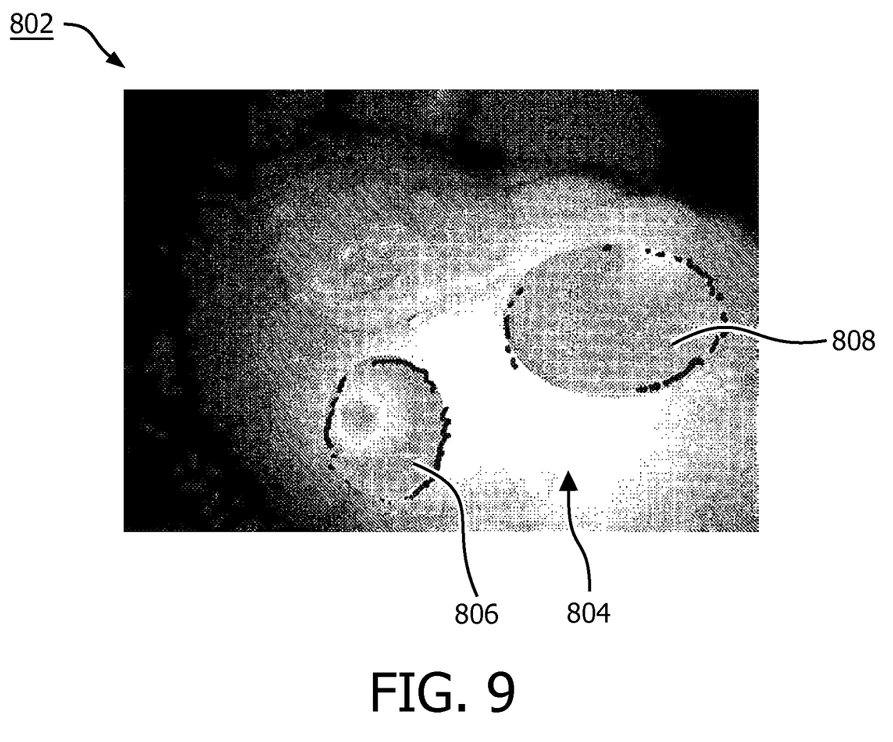
FIG. 9 is a real-time image showing an overlay map with unacceptable sites for deploying a medical device in accordance with another illustrative embodiment.

Referring to FIG. 9, an illustrative endoscopic image 802 is depicted. Image 802 includes a visual depiction of a heart 804 and danger zones 806 and 808 corresponding to high risk areas where critical anatomy is present that needs to be avoided by an injection needle or the like. These structures or regions 806, 808 can be identified based on patient specific information, from pre-procedural imaging or from anatomical libraries of such information that can be mapped into the patient-specific coordinate space visualized endoscopically. Regions 806 and 808 may be digitally mapped onto the heart surface 804 (or other organ or tissue surface) to be displayed on a display (e.g., display 118 of FIG. 1) to permit visualization by a physician or other user. The information for danger zones 806, 808 may be employed in a procedural confidence/complication spatial map which may be employed as input to computer-aided path planning and procedure optimization. The path plan may be executed in a (semi)automated process based on control of a robotic actuation mechanism(s) of the tools employed in the procedure.

Figure 10:
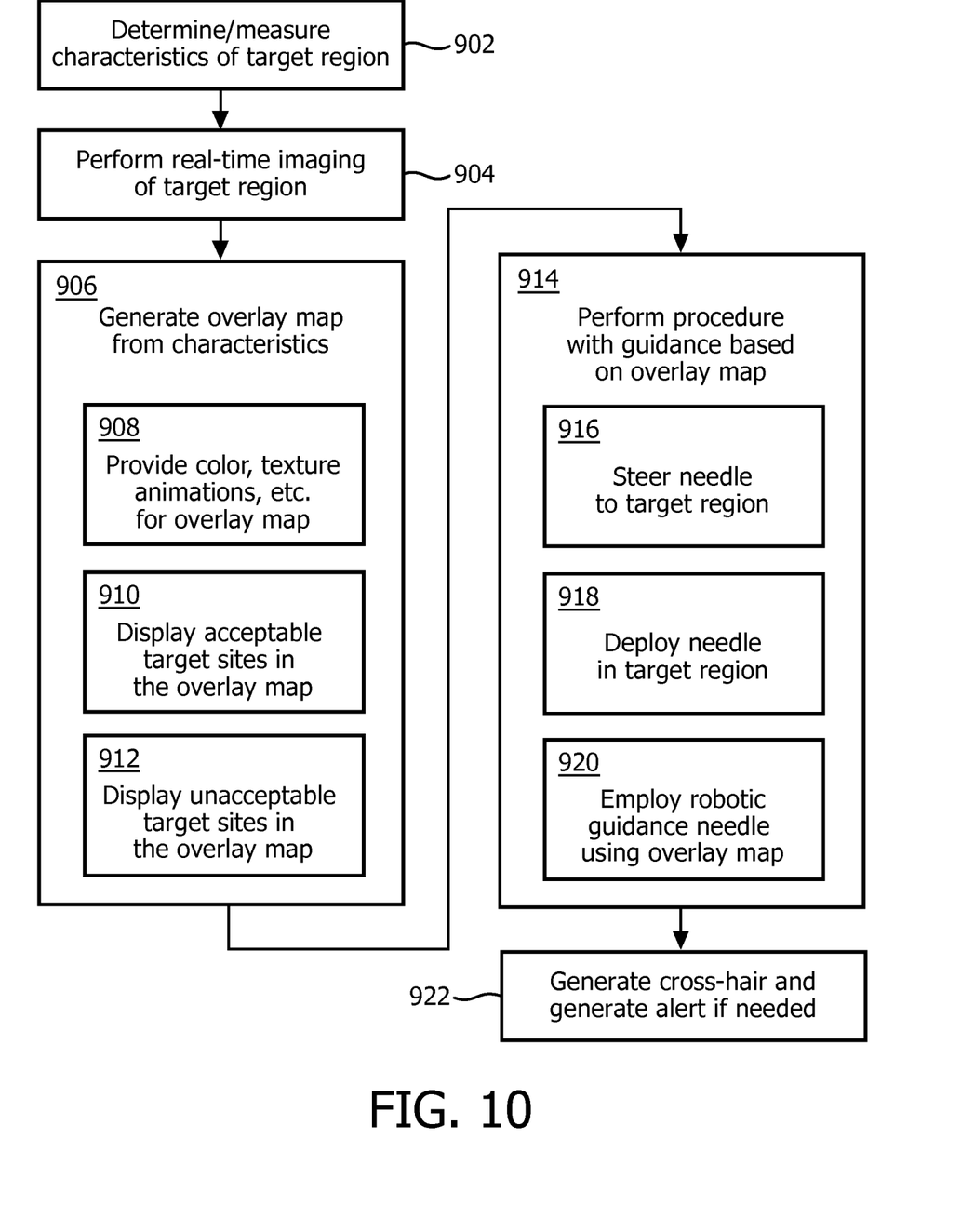
FIG. 10 is a block/flow diagram showing a system/method for guidance in accordance with an overlay map of tissue characteristics in accordance with another illustrative embodiment.

Referring to FIG. 10, a method for device guidance is depicted in accordance with another embodiment. In block 902, characteristics of interest are determined or measured for a target region of a patient. The characteristics may be any feature and may include, e.g., tissue thicknesses, scar tissue locations, tissue density, etc. In block 904, real-time imaging is performed of the target region to provide a real-time image. The real-time image will serve as a background or base image for an overlay as will be described.

In block 906, an overlay map is generated and registered to the real-time image on a display or other rendering to project morphological feature information on corresponding features in the real-time image of the target region. The morphological feature information may be collected from the target region pre-operatively or intra-operatively using an imaging system. The overlay map includes pixel values indicative of information about the corresponding tissue being imaged. In this way, the overlay map indicates the measured feature values so that a physician, other user or computer device can make determinations of a best location or locations for carrying out a procedure. In block 908, the overlay map may include color or texture variations, animations, etc. to indicate variations in morphological feature information. In block 910, the overlay map may include displaying acceptable injection sites and/or targets or cross-hairs for assisting in aiming devices. In block 912, the overlay map may display danger zones where injections should not occur.

In block 914, a procedure is performed on the target region such that at least one medical instrument is guided to a region suitable for performing an operative task based upon the overlay map. The target region may include a heart and the morphological feature information may include at least one of wall thickness and scar tissue on the heart and the step of performing a procedure may include steering a needle to the target region in block 916 and deploying the needle into the target region in accordance with the overlay map in block 918.

In block 920, the procedure may include robotic guidance of a medical instrument to the target region using the overlay map to control guidance to an operable site. The robot may also be employed to deploy the instrument in accordance with the overlay map. In one embodiment, a user may plan orientation and depth of the at least one medical instrument and the robot inserts the at least one medical instrument into an organ. In another embodiment, a user may plan orientation and depth of the medical instrument, the robot orients the instrument, the user inserts the instrument (e.g., a needle), the robotic system measures the depth, and the imaging device/visualization system shows a current depth in real time. In yet another embodiment, the user plans orientation and depth of the instrument, the robot orients the instrument, the user inserts the instrument (e.g., needle), the robotic system measures the force via a force sensor, and the visualization system shows current insertion force in real time. In another embodiment, the user plans orientation and depth of the instrument, the robot orients and inserts the instrument, the robotic system measures the force via a force sensor, and the force information is used in a closed loop control system to control depth using real time force information. Other combinations of robotic and manual collaboration are also contemplated.

In block 922, a cross-hair or other symbol may be generated in the real-time image for aiming the at least one medical instrument, and an alert may be triggered when the cross-hair is aimed at a risk area as indicated by the overlay map.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and     e) no specific sequence of acts is intended to be required unless specifically indicated.

Having described preferred embodiments for systems and methods for guided injection during endoscopic surgery (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A guidance system, comprising:
a real-time imaging device configured to pre-operatively or intra-operatively collect image data of a target region to provide a pre-operative or real-time image;
a target determination module configured to convert the pre-operative or real-time image data of the target region including a heart into a morphological map registered to the pre-operative or real-time image to project morphological feature information including wall thickness of the heart, or scar tissue on the heart, or both, on corresponding features in the real-time image of the target region, the morphological map comprising a danger zone denoting a high risk area where critical anatomy is located; and
at least one medical instrument configured to perform a procedure on the target region such that the at least one medical instrument is guided to a region suitable for performing an operative task based upon the morphological map, the at least one medical instrument being configured to perform the operative task based on the morphological feature information.

2. The guidance system as recited in claim 1, wherein the real-time imaging device includes an endoscope with a camera.

3. The guidance system as recited in claim 1, wherein the morphological map includes one of color and texture variations to indicate variation in the wall thickness, or scar tissue, or both, on the heart.

4. The guidance system as recited in claim 1, wherein the at least one medical instrument includes a needle and the morphological map shows acceptable injection sites.

5. The guidance system as recited in claim 1, wherein the at least one medical instrument is guided using a robot and the robot is controlled based upon the morphological map.

6. The guidance system as recited in claim 5, wherein the robot inserts the at least one medical instrument into an organ.

7. The guidance system as recited in claim 5, wherein the robot measures an insertion depth of a needle of the at least one medical instrument, and a display indicates a current insertion depth in real-time.

8. The guidance system as recited in claim 5, wherein the robot measures an insertion force of a needle of the at least one medical instrument using a force sensor, and a display indicates a current insertion force in real-time.

9. The guidance system as recited in claim 8, wherein information on the insertion force is employed in a closed loop control system to control insertion depth.

10. The guidance system as recited in claim 1, wherein the morphological feature information is collected from the target region pre-operatively or intra-operatively using an imaging system.

11. A workstation, comprising:
a processor;
memory coupled to the processor;
a real-time imaging device configured to intra-operatively collect image data of a target region including a heart to provide a real-time image;
a target determination module stored in the memory and configured to generate: a morphological map registered to the real-time image on a display to project morphological feature information including wall thickness of the heart, or scar tissue on the heart, or both, on corresponding features in the real-time image of the target region, the morphological map comprises a danger zone denoting a high risk areas where critical anatomy is located; and
at least one medical instrument manually or automatically controlled to perform a procedure on the target region such that the at least one medical instrument is guided to a region suitable for performing an operative task based upon the morphological map.

12. The workstation as recited in claim 11, wherein the real-time imaging device includes an endoscope with a camera.

13. The workstation as recited in claim 11, wherein the morphological map includes one of color and texture variations to indicate variations in the wall thickness, or scar tissue, or both, on the heart.

14. The workstation as recited in claim 11, wherein the at least one medical instrument includes a needle and the morphological map shows acceptable injection sites.

15. The workstation as recited in claim 11, wherein the at least one medical instrument is guided using a robot and the robot is controlled based upon the morphological map.

16. The workstation as recited in claim 15, wherein the robot inserts a needle of the at least one medical instrument into an organ and measures at least one of an insertion depth and insertion force of the needle.

17. The workstation as recited in claim 16, wherein a display indicates the at least one of insertion depth and insertion force in real-time.

18. The workstation as recited in claim 16, wherein information on the insertion force is employed in a closed loop control system to control insertion depth.

19. The workstation as recited in claim 11, wherein the morphological feature information is collected from the target region pre-operatively or intra-operatively using an imaging system.

20. The workstation as recited in claim 11, wherein the target determination module generates a cross-hair in the real-time image for aiming the at least one medical instrument.

21. The workstation as recited in claim 20, further comprising a warning mechanism configured to provide an alert when the cross-hair is aimed at a risk area as indicated by the morphological map.

22. A method, comprising:
determining characteristics of interest for a target region of a patient;
real-time imaging the target region including a heart to provide a real-time image;
generating a morphological map registered to the real-time image on a display to project morphological feature information including wall thickness of the heart, or scar tissue on the heart, or both, on corresponding features in the real-time image of the target region, the morphological map comprising a danger zone denoting a high risk area where critical anatomy is located; and
performing a procedure on the target region such that at least one medical instrument is guided to a region suitable for performing an operative task based upon the morphological map.

23. The method as recited in claim 22, wherein the step of performing a procedure comprises:
steering a needle to the target region; and deploying the needle into the target region in accordance with the morphological map.

24. The method as recited in claim 22, wherein generating a morphological map includes generating the morphological map to include one of color and texture variations to indicate variations in morphological feature information.

25. The method as recited in claim 22, wherein generating a morphological map includes displaying acceptable injection sites.

26. The method as recited in claim 22, wherein performing a procedure includes robotically guiding the at least one medical instrument to the target region using the morphological map to control guidance to an operable site.

27. The method as recited in claim 22, wherein the morphological feature information is collected from the target region pre-operatively or intra-operatively using an imaging system.

28. The method as recited in claim 22, further comprising generating a cross-hair in the real-time image for aiming the at least one medical instrument, and alerting when the cross-hair is aimed at a risk area as indicated by the morphological map.

29. The method as recited in claim 22, wherein real-time imaging includes imaging at least one of insertion depth and an insertion force achieved by the at least one medical instrument.

30. The method as recited in claim 29, wherein information on the insertion force is employed in a closed loop control system to control insertion depth.

* * * * *